United States Patent [19]

Cherkofsky et al.

[11] 4,215,135
[45] Jul. 29, 1980

[54] ANTIINFLAMMATORY 2-SUBSTITUTED-1H-PHENANTHRO[9,10-D]IMIDAZOLES

[75] Inventors: Saul C. Cherkofsky, Wilmington, Del.; Thomas R. Sharpe, Fort Salonga, N.Y.

[73] Assignee: E. I. Du Pont de Nemours and Company, Wilmington, Del.

[21] Appl. No.: 45,671

[22] Filed: Jun. 8, 1979

Related U.S. Application Data

[63] Continuation-in-part of Ser. No. 948,035, Oct. 2, 1978, abandoned.

[51] Int. Cl.² .................. A61K 31/415; C07D 235/28
[52] U.S. Cl. .................. 424/273 B; 260/340.2; 260/351; 548/305; 548/326; 548/337; 548/346
[58] Field of Search .................. 548/326; 424/273 B

[56] References Cited

U.S. PATENT DOCUMENTS

| | | | |
|---|---|---|---|
| 3,480,643 | 11/1969 | Lutz et al. | 548/329 |
| 3,505,350 | 4/1970 | Doebel et al. | 548/337 |
| 3,636,003 | 1/1972 | Doebel et al. | 548/337 |
| 3,651,080 | 3/1972 | Doebel et al. | 548/337 |
| 3,707,475 | 12/1972 | Lombardino | 548/342 |
| 3,711,489 | 1/1973 | Lombardino | 548/323 X |
| 3,781,294 | 12/1973 | Lombardino | 548/323 X |
| 3,920,681 | 11/1975 | Buchel et al. | 548/329 |

FOREIGN PATENT DOCUMENTS

| | | | |
|---|---|---|---|
| 1516908 | 7/1978 | United Kingdom . | |
| 487073 | 10/1975 | U.S.S.R. | 548/337 |

OTHER PUBLICATIONS

Lombardino, J., *J. Met. Chem.*, 11, 17 (1974).
Lombardino, J., et al., *J. Med. Chem.*, 17, 1182 (1974).
Fetter et al. Acta Chim. Acad. Sci. Hung. 1973, vol. 79, pp. 197–212.
Fetter et al. Tetrahedron 1971, vol. 27, pp. 5933–5941.
Eptein Chem,. Abst. 1954, vol. 48, col. 8204–8205.
Bhatt et al. Current Science 1948, vol. 17, pp. 184–185.
Skvortsova et al. Chem. Abst. 1976, vol. 84, No. 59472t.
Yagupol'skli et al. Chem. Abst. 1960, vol. 54, col. 11000–11001.
Zauer et al. Chem. Ber. 1973, vol. 106, pp. 1628–1636.

*Primary Examiner*—Natalie Trousof

[57] ABSTRACT

Certain 2-substituted-1H-phenanthro[9,10-d]-imidazoles such as 2-[(1,1,2,2-tetrafluoroethyl)-sulfonyl]-1H-phenanthro[9,10-d]imidazole, are useful as antiinflammatory agents.

21 Claims, No Drawings

ANTIINFLAMMATORY 2-SUBSTITUTED-1H-PHENANTHRO[9,10-D]IMIDAZOLES

CROSS REFERENCE TO RELATED APPLICATIONS

This application is a continuation-in-part of application Ser. No. 948,035, filed Oct. 2, 1978, now abandoned.

BACKGROUND OF THE INVENTION

This invention is directed to a novel class of phenanthro-imidazole compounds and to the use of those compounds an antiinflammatory agents.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial anti-inflammatories is limited because of toxicity and adverse side-effects. Many produce gastric irritation and other effects, such as changes in blood cells and central nervous system. Adreno-cortical steroids produce gastric irritation and suppression of normal adrenal function.

The *Journal of the American Medical Association*, Vol. 224, No. 5 (Supplement), 1973 "Primer on the Rheumatic Diseases" states that "Immunologic reactions appear to play a major role in the perpetuation of rheumatoid inflammation." Widely used non-steroidal anti-inflammatory drugs, such as aspirin, indomethacin, phenylbutazone and ibuprofen have no effect on these immunologic reactions, but merely relieve the symptoms of the inflammatory response; these drugs do not stop the progressive and ultimately destructive processes of rheumatoid arthritis. Immunosuppressive drugs, such as cyclophosphamide, are effective in the treatment of rheumatoid arthritis, but are too toxic for widespread use.

The present invention results from efforts to develop new anti-arthritic compounds with good anti-inflammatory and immunoregulatory activity and minimal side effects that could be more effective in treating arthritis than presently available drugs.

In addition to antiinflammatory properties, compounds within the scope of this invention have demonstrated analgesic activity in a test procedure. This additional property is desirable in treatment of arthritis or related diseases; however, the compounds which exhibit this property can be employed solely to alleviate pain.

BRIEF SUMMARY OF THE INVENTION

The invention is therefore directed to a novel class of 2-substituted-phenanthro[9,10-d]imidazoles corresponding to the formula:

(I)

wherein
$n = 0-2$
$R_1 = -CF_2H$, $-CF_3$ or $-CF_2CH_mF_{3-m}$ in which $m = 0-3$
$R_2 = -H$, $$-\underset{R_3}{\underset{|}{C}}HOR_4,$$

2-tetrahydropyranyl, 2-tetrahydrofuranyl, $-COR_5$, $-CR_5$, $-C(=O)-\text{phenyl}(Y_3)$ or $-SO_2-\text{phenyl}(Y_3)$;

provided when $R_2 =$ $-COR_5$, $-C(=O)-R_5$, $-C(=O)-\text{phenyl}(Y_3)$ or $-SO_2-\text{phenyl}(Y_3)$, then n must be 0;
$R_3 = -H$ or $-CH_3$;
$R_4 = C_{1-3}$ alkyl, benzyl, $-CH_2CH_2OCH_3$ or $-CR_5$ (C=O);

$R_5 = C_{1-4}$ alkyl or benzyl;
$X_1$ and $Y_1$ are independently selected from the group consisting of $-H$, $-F$, $-Cl$, dimethylamino and $C_{1-2}$ alkoxy;
$X_2$ and $Y_2$ are independently selected from the group consisting of $-H$, $-F$ and $-Cl$;
$Y_3$ is $-H$, $-F$, $-Cl$, $-Br$, $C_{1-4}$ alkyl, $C_{1-4}$ alkoxy or $-NO_2$;
and,
when $R_2 = -H$, a pharmaceutically suitable acid salt when $n = 0$ or pharmaceutically suitable metal salts when $n = 1-2$.

The invention is also directed to pharmaceutical compositions containing the above-described compounds and to the method of using them as anti-inflammatory agents.

Lombardino, in U.S. Pat. No. 3,707,475 discloses anti-inflammatory 4,5-diaryl-2-substituted imidazoles.

Doebel, in U.S. Pat. Nos. 3,505,350 and 3,651,080, respectively, discloses anti-inflammatory 4-alkyl-5-aryl-1-substituted-2-mercapto imidazoles and 4-alkyl-2-alkylthio-5-aryl-1-substituted imidazoles.

Zauer, K., et al., in *Chem. Ber.* 106, 1638 (1973), disclose 4,5-bis(4-methoxyphenyl)-2-methylthioimidazole and 4,5-bis(4-chlorophenyl)-2-methylthioimidazole but do not suggest any use.

A number of references, such as *Current Sci. India* 17, 184–85 (1948) and *Acta. Chem. Acad. Sci. Hung.* 79 (2) 197–212 (1973) disclose 2-(substituted-thio)-4,5-diphenyl imidazoles and 1-methyl-2-(substituted thio)- 4,5-diphenyl imidazoles with substituents such as methyl, propyl, allyl, and acetonyl.

Copending U.S. patent application Ser. No. 876,864, filed Feb. 10, 1978 in the names of Cherkofsky and Sharpe discloses anti-inflammatory 4,5-diaryl-2-(substituted-thio)imidazoles corresponding to the general formula

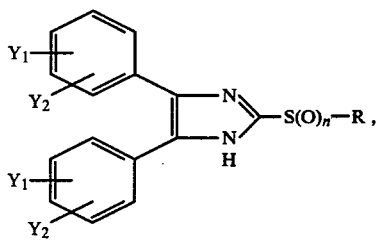

wherein n=0–2 and R includes $C_{1-8}$ polyhaloalkyl groups.

DETAILED DESCRIPTION OF THE INVENTION

Within the content of the formula given above, certain structural variations of the 2-substituted-phenanthro[9,10-d]imidazoles of the invention are preferred. The preferred compounds are those in which independently:

(a) n=2;

(b) $R_1$=—$CF_3$ or —$CF_2CF_2H$;

(c) $R_2$=—H;

(d) $X_1$ and $Y_1$ are independently selected from the group consisting of —H, —F, —Cl and —$OCH_3$, provided, however, that both cannot be —H;

(e) $X_2$ and $Y_2$=H.

When $R_2$=H and $X_1$ and $Y_1$ and/or $X_2$ and $Y_2$ are different the following two structures are tautomers.

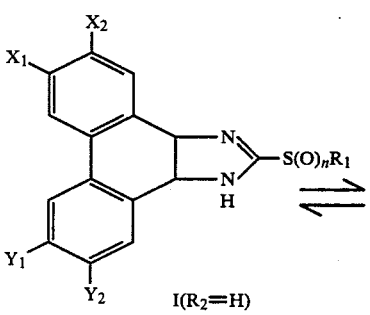

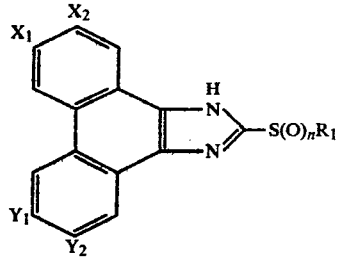

Preferred pharmaceutically suitable acid salts are those formed from mineral acids such as hydrochloric, sulfuric, and nitric acids. The acid preferably has a pKa value no higher than about 2.5. Pharmaceutically suitable metal salts are those of the alkali and alkaline earth metals, especially sodium, potassium and calcium.

Synthesis

The compounds of the invention can be made by the following sequence of reactions:

(1) Quinone Condensation

Phenanthrene-9,10-quinone or an appropriately substituted analog is reacted with hexamethylenetetramine (hexamine) and ammonium acetate in glacial acetic acid to produce the corresponding phenanthro[9,10-d]imidazole. The reaction is carried out with refluxing of the acetic acid.

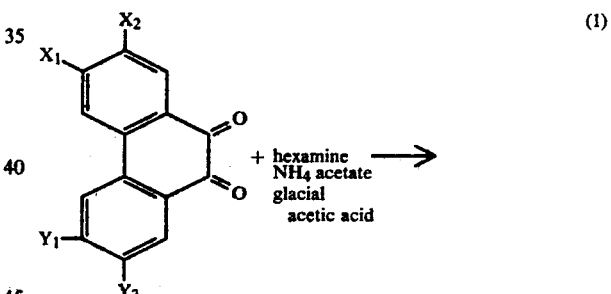

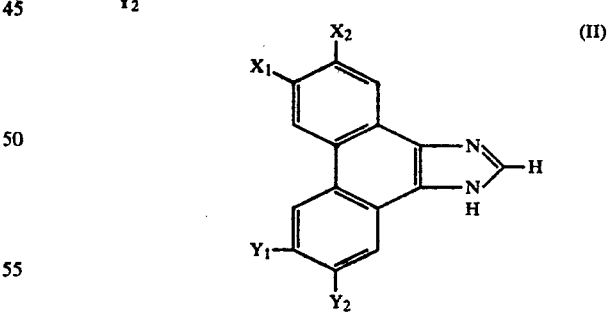

[Edgar A. Stock and A. R. Day, *J. Am. Chem. Soc.*, 65, 452 (1943)].

(2) Sulfur Insertion

The phenanthroimidazole from Reaction (1) is then converted to the corresponding 2-mercapto derivative by treating it with finely divided sulfur using sulfolane as solvent for the systems. The reaction is carried out using a slight excess of sulfur at a temperature of over 200° C.

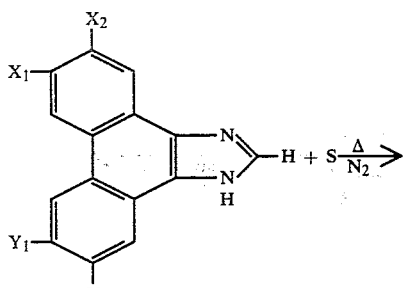

(II)

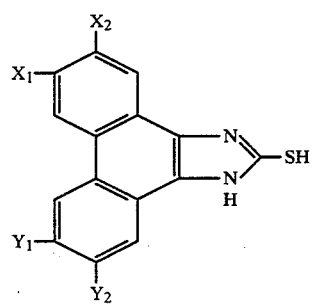

(III)

[A. V. Elstov and K. M. Krivozheiko, *ZhOrKm*, 2, 189 (1966)].

(3) Alkylation

The appropriate $R_1$ moiety can then be introduced onto the sulfur by a suitable alkylating agent such as tetrafluoroethylene or difluorocarbene. For example, the 2-mercaptoimidazole derivative of Reaction (2) can be reacted with tetrafluoroethylene to form the 2-(1,1,2,2-tetrafluoroethylthio)imidazole derivative.

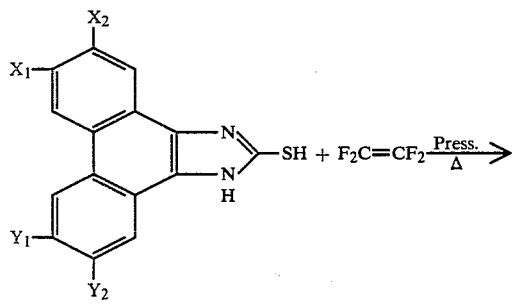

(III)

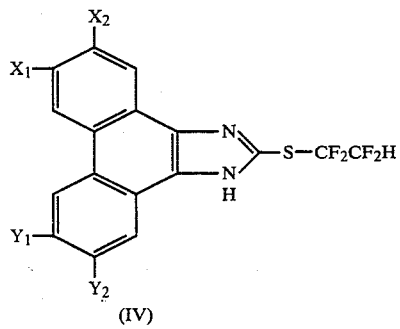

(IV)

The reaction is carried out under heat and pressure with a slight excess of the fluorocarbon reactant. Typically, the reaction is carried out in a closed reaction vessel at a temperature of 50° C. at an initial pressure of about 50 p.s.i. which falls to about 13 p.s.i. as the reaction proceeds. Similar addition reactions of tetrafluoroethylene and other fluorinated olefins are described by England, D. C. et al., *J. Am. Chem. Soc.*, 82, 5116 (1960) and Rapp, K. E., et. al., *J. Am. Chem. Soc.*, 72, 3642 (1950). Within the context of the invention, tetrafluoroethylene and other fluorinated olefins used are considered alkylating agents.

In certain instances, a polyhaloalkyl moiety can be further modified chemically in forming the $R_1$ constituent. For example, imidazoles containing the 2-(2-bromo-1,1,2-trifluoroethylthio) substituent can be converted to 2-(1,1,2-trifluoroethylthio)imidazoles by reduction with tri-n-butyltin hydride or other suitable reducing agents.

(4) Oxidation

The 2-(substituted-thio)imidazole compound from Reaction (3) can then be oxidized to the corresponding sulfoxide or sulfone by using oxidizing agents such as m-chloroperbenzoic acid (m-CPBA)

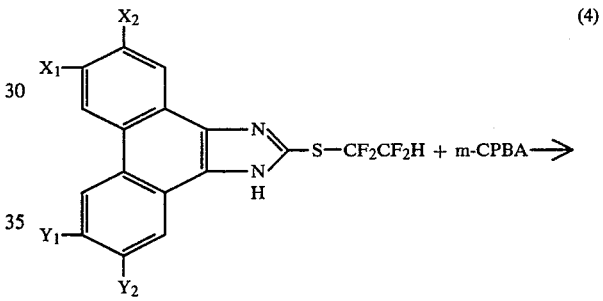

(IV)

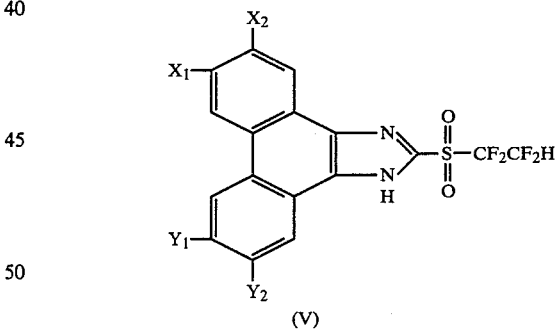

(V)

[Tweit, R. C., et al., *J. Med. Chem.*, 16, 1161 (1973)].

Other suitable oxidizing agents include sodium metaperiodate [Leonard, N. J. and Johnson, C. R., *J. Org. Chem.* 27, 282 (1962)], hydrogen peroxide [Kochergin, P. M. and Shchukina, M. N., *J. Gen. Chem. U.S.S.R*, 25, 2289 (1955)] and potassium permanganate [Rapp, K. E. et al., *Loc cit*].

(5) Variations in $R_2$—First Method

The appropriate $R_2$ substituent on the imidazole ring of the compounds of the invention can often be introduced by direct alkylation, acylation or sulfonylation of the compound of Formula I where $R_2$ is H.

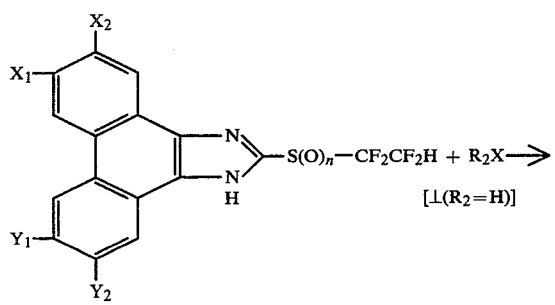

[I(R₂=H)]

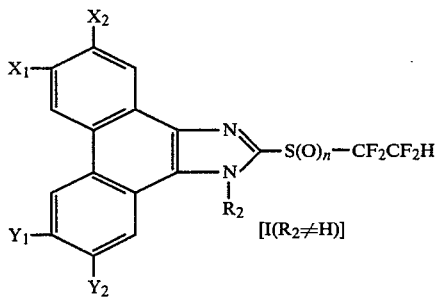

[I(R₂≠H)]

This reaction can be carried out in the absence or presence of a base, such as potassium carbonate, pyridine, triethylamine, potassium t-butoxide, methyl lithium or the like. The reaction can be run neat, using the reagent as solvent, or in the presence of an inert solvent, including but not limited to dimethylformamide, glyme, tetrahydrofuran, pyridine and methylene chloride. The temperature of the reaction can be in the range from about −78° C. to the boiling point of the solvent or reagent. Examples of alkylating, acylating and sulfonylating agents that can be employed are the following: alkoxymethyl halides, such as benzyloxymethyl chloride; acyloxymethyl halides, such as chloromethylpivalate; dihydropyran; ethyl vinyl ether; 2-chlorotetrahydrofuran; alkyl chloroformates, such as ethyl chloroformate; alkanoic anhydrides and alkanoyl halides, such as acetic anhydride; aroyl halides, such as benzoyl chloride; arylsulfonyl halides, such as benzenesulfonyl chloride.

(6) Variations in R₂—Second Method

Alternatively, the R₂ substituents other than hydrogen can be introduced by first reacting a phenanthroimidazole with an appropriate reagent such as benzyl chloromethyl ether, 2-chlorotetrahydrofuran, dihydropyran, ethyl vinyl ether, or benzenesulfonyl chloride. The resulting 1-(substituted)phenanthro imidazole is then treated with a strong base, such as n-butyl lithium, followed by a fluorinated alkylsulfenyl halide, disulfide, or sulfonic anhydride. Typical of these reagents are CF₃SCl, CF₃SSCF₃, and (CF₃SO₂)₂O. Optionally, the choice of the protecting group and the workup conditions allows isolation of the 2-(substituted-thio or -sulfonyl)phenanthro[9,10-d]imidazole with R₄=H directly. Compounds where R₁=CF₃ can be conveniently prepared by this method.

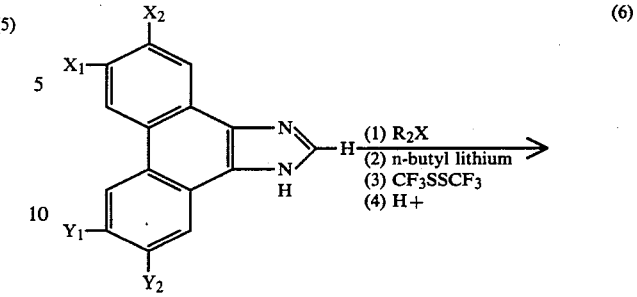

(II)

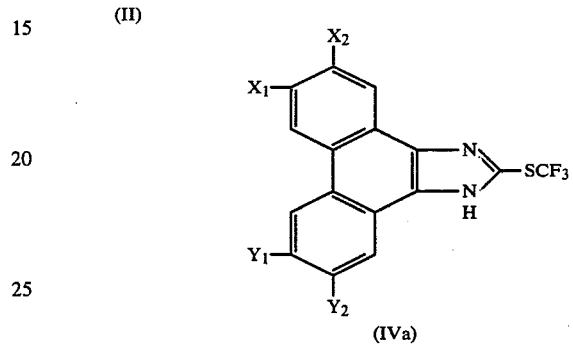

(IVa)

(7) Alternative Synthesis Method—Compound (II)

In addition to the condensation method illustrated above, the intermediate phenanthroimidazoles (Compound II) can also be obtained by the photochemical cyclization of 4,5-diarylimidazoles having appropriate substituents, as follows:

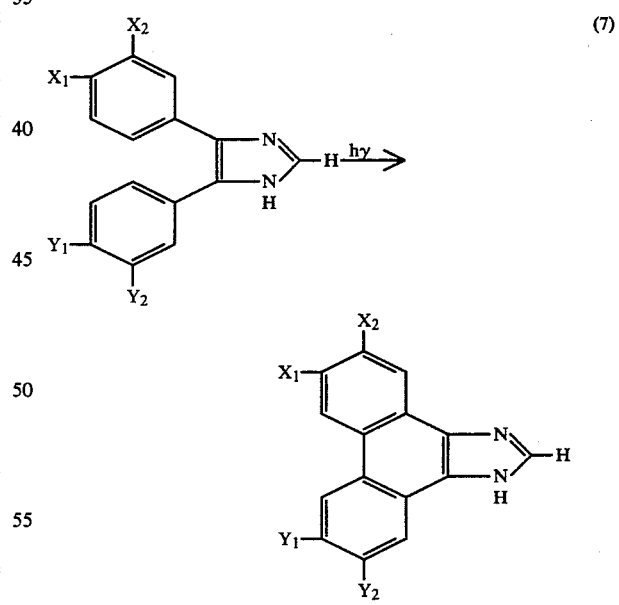

[Copper, J. L., and Wasserman, H. H., *Chem. Comm.*, 200, (1969)].

The phenanthroimidazoles thus obtained can be converted further by the above sequence of Reactions (2)–(6).

(8) Synthesis of Phenanthrene-Quinone

The phenanthrene-quinone starting material used as a reactant in Reaction (1) can be obtained by photochemical cyclization of the appropriately substituted stilbene to form the corresponding phenanthrene (Reaction 8A) which in turn is oxidized to the required 9,10-quinone starting material (Reaction 8B).

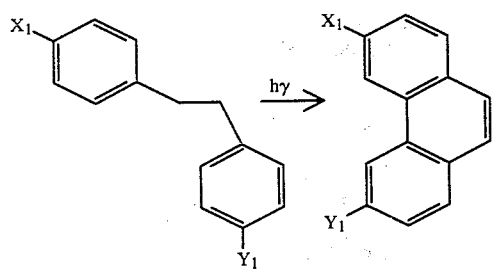
(8A)

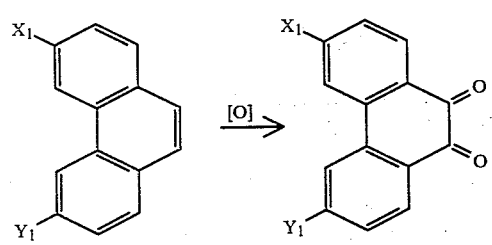
(8B)

These phenanthrene[9,10]quinones can then be used in the sequence of Reactions (1) through (6) to produce the compounds of the invention.

(9) Synthesis of Phenanthrene-Quinone—Alternative Method

Another route to obtain the phenanthrene[9,10]quinones is conversion of the appropriately substituted benzoin to a 1,2-diarylvinylidene carbonate (Reaction 9A) followed by photocyclization of the carbonate to the phenanthrene (Reaction 9B) and oxidation of the phenanthrene to the quinone (Reacton 9C).

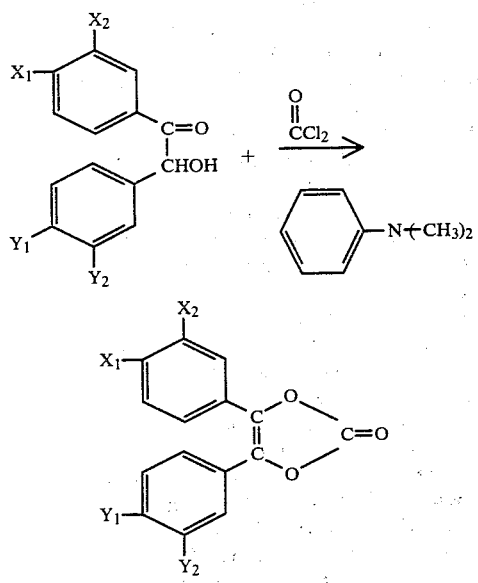
(9A)

[Sheehan, J. C., and Guziec, F. S., *J. Org. Chem.*, 38, 3035 (1973)].

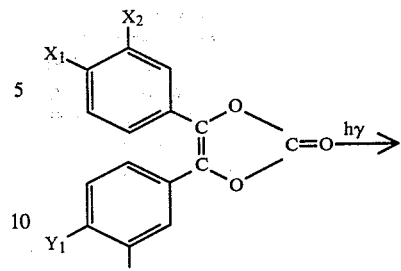
(9B)

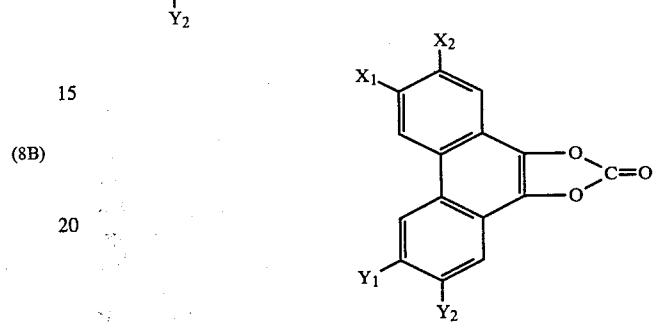

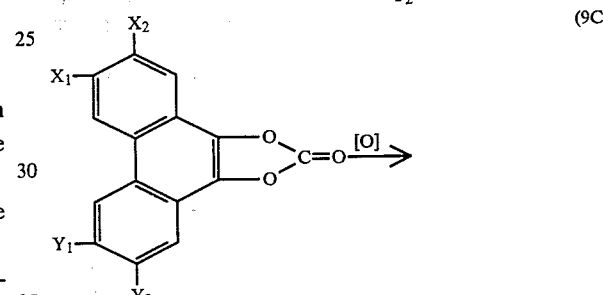
(9C)

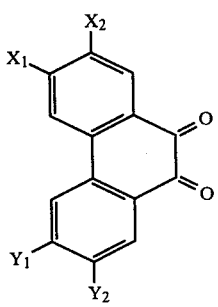

[Lantos, I., *Tet. let.*, 31, 2761 (1978)].

The resultant 9,10-quinone can then be used to synthesize the claimed invention compounds by the sequence of Reactions (1) through (6)

The compounds of the invention and their synthesis are illustrated further by the following examples in which all percentages, including compositional analyses, are by weight and all temperatures in degrees celsius.

EXAMPLE 1

1H-Phenanthro[9,10-d]imidazole-2-thiol

Phenanthro[9,10-d]imidazole was obtained according to the procedure described by Stock and Day, *J. Am. Chem. Soc.*, 65, 452(1943).

Ten grams of the imidazole was suspended in 100 ml of sulfolane (tetramethylene sulfone) and 3 gms of powdered sulfur was added; the resulting mixture was heated in an atmosphere of nitrogen at 200°–205° with thorough stirring for eight hours. The reaction mixture was then cooled, and diluted with 500 ml of ice-cold water. The dark brown mass that separated was collected by filtration and thoroughly washed with water and dried in a vacuum oven at 100° for ten hours. The crude product was purified by column chromatography using basic alumina (Woelm grade 1) and dimethylformamide as the eluent. The purified product was triturated with boiling acetonitrile, melting point above 375°.

EXAMPLE 2

2-[(1,1,2,2-tetrafluoroethyl)thio]-1H-phenanthro[9,10-d]imidazole

Six grams of the above-described thioimidazole (Example 1) was suspended in 100 ml of dimethylformamide and 3.5 ml of diisopropylamine added; the mixture was placed in a stainless steel pressure reaction vessel, evacuated several times by purging with nitrogen and finally 4.8 gms of tetrafluoroethylene metered in. The mixture was heated in a closed system to 50° for eight hours. The reaction mixture was cooled and then poured into 1000 ml of water. A gelatinous mass separated, which was collected by filtration, thoroughly washed with water and dried. The product, recrystallized from benzene, melted at 230°–31°.

Anal. Calc. for $C_{17}H_{10}F_4N_2S$: C, 58.37; H, 2.87; N, 7.99; F, 21.69; S, 9.15.

Found: C, 58.01; H, 3.03; N, 7.89; F, 21.54; S, 9.53.

EXAMPLE 3

2-[(1,1,2,2-Tetrafluoroethyl)sulfonyl]-1H-phenanthro[9,10-d]-imidazole

To a suspension of 2-[(1,1,2,2-tetrafluoroethyl)-thio]-1H-phenanthro[9,10-d]imidazole (3.5 gms, 0.01 mole) in 75 ml of chloroform, a solution of m-chloroperoxybenzoic acid (86.4%; 4.47 gms; 0.022 mole) in chloroform (50 ml) was gradually added, and the mixture was heated under reflux for 24 hours. The cooled reaction mixture was diluted with more chloroform, washed with saturated sodium bicarbonate solution and then with water, and dried over anhydrous magnesium sulfate. Evaporation of the filtered chloroform solution gave a residue, which on recrystallization from benzene, gave the product (2.8 gm) which melted at 254°–256°.

EXAMPLE 4

6,9-Dimethoxy-1H-phenanthro[9,10-d]imidazole

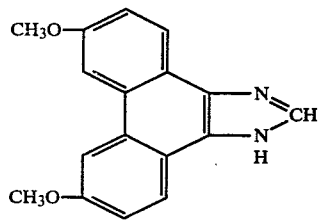

A solution of 4,5-bis(4-methoxyphenyl)imidazole in absolute ethanol[3.5 gms (0.0125 mole) in 800 ml absolute ethanol, 140 mg iodine as catalyst] was photolysed using a 450 watt Havovia lamp, and a Vycor filter for four hours.

The combined photolysates from six phiotocyclizations were combined, and recrystallized from ethanol. The initial crop yielded 5.1 gms of product which melted at 231°–234°. Additional amount of product was obtained by column chromatographic separation.

Anal. Calc. for $C_{17}H_{14}N_2O_2$: C, 73.36; H, 5.07; N, 10.07. Found: C, 73.4; H, 5.38; N, 9.94.

EXAMPLE 5

6,9-Dimethoxy-2-(trifluoromethylthio)-1H-phenanthro[9,10-d]-imidazole

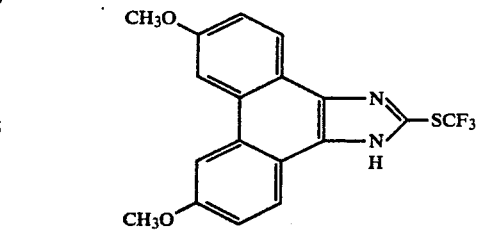

(a) 6,9-Dimethoxy-1-(1-ethoxyethyl)-1H-phenanthro[9,10-d]-imidazole:

A suspension of 6,9-dimethoxy-1H-phenanthro[9-10-d]imidazole (8.4 gms) in toluene (200 ml) was treated with ethyl vinyl ether (15 ml), followed by dichloroacetic acid (3.9 gms). The mixture was heated under gentle reflux for 1 hour; solution occurs after thirty minutes. The reaction mixture was cooled, diluted with 200 ml more toluene, and 100 ml 25% aqueous sodium hydroxide added, and stirred overnight. The organic phase was separated, washed several times with water, dried over anhydrous potassium carbonate. The inorganic salts were filtered off and the crude product examined by thin layer chromatography using 50 parts tetrahydrofuran and 50 parts toluene.

The product was purified by column chromatography using basic alumina, and tetrahydrofuran and toluene (50:50). Infrared spectrum of the purified sample showed no ester group.

(b) 6,9-Dimethoxy-2-(trifluoromethylthio)-1H-phenanthro[9,10-d]imidazole:

To a solution of 10.5 g (0.03 mole) of 6,9-dimethoxy-1-(1-ethoxyethyl)-1H-phenanthro[9,10-d]imidazole and 4.6 g (0.04 mole) of N,N,N',N'-tetramethylethylenediamine in 150 ml ether at −78° was added dropwise 25 ml (0.035 mole) of 1.4 M n-butyl lithium solution in hexane. The reaction mixture was stirred another 15 minutes at −78°, then a solution of 7.0 g (0.035 mole) of bistrifluoromethyldisulfide (TOXIC) in 25 ml ether was added dropwise. The mixture was stirred at −78° one hour, then 110 ml of saturated aqueous sodium bicarbonate was added dropwise. The mixture was stirred overnight at room temperature, then diluted with more saturated aqueous sodium bicarbonate and extracted with ether. The ether extracts were dried and concentrated to give 13.5 g of an amber oil. This oil was dissolved in 150 ml ethanol and 30 ml 1 N hydrochloric acid was added. The mixture was stirred for one hour, then diluted with water and the precipitated solid was collected, washed with water, then hexane, then air dried to give 7.5 g of crude brown product. The crude product was purified by chromatography on 300 g silica gel, eluting with mixtures of toluene and ethyl acetate (5–10% ethyl acetate), to give, after recrystallization from ethanol/water, 4.5 g of product, mp 201°–202.5° (polymorphic form mp ~ 160°). The ir, proton and fluorine nmr spectra were all consistent with the desired structure.

Mass spectrum: Calcd: 378.0647; Found: 378.0643.
Anal. calcd. for $C_{18}H_{13}F_3N_2O_2S$: C, 57.14; H, 3.46; N, 7.40. Found: C, 56.86; H, 3.61; N, 7.28.

EXAMPLE 6

6,9-Dimethoxy-2-(trifluoromethylsulfonyl)-1H-phenanthro-[9,10-d]imidazole

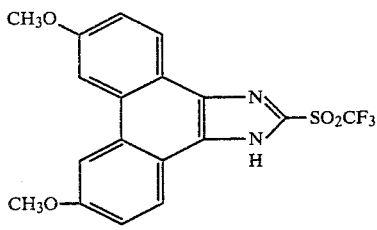

To a solution of 1.9 gms of the trifluoromethylthio compound (Example 5) in 100 ml of methylene chloride was added m-chloroperoxybenzoic acid (2.5 gms), and the mixture was refluxed for twenty-four hours. The reaction mixture turns extremely dark purple. The excess oxidizing agent was removed by adding methyl sulfide (1 ml), and the acidic components removed by extraction with dilute sodium bicarbonate solution and the organic phase washed with water. The crude product was isolated by evaporating the solvent; purification was effected by column chromatography on silica gel using toluene (80%) and ethyl acetate (20%); recrystallized from toluene, m.p. 228°–231°.

EXAMPLE 7

6,9-Difluoro-2-[(1,1,2,2-tetrafluoroethyl)thio]-1H-phenanthro-[9,10-d]imidazole

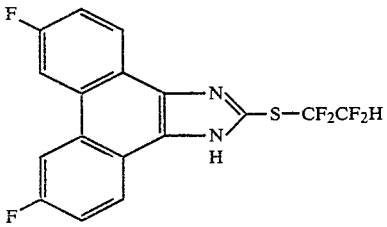

(a) 6,9-Difluoro-1H-phenanthro[9,10-d]imidazole:

The subject compound was prepared by photocyclization, carried out as described in Example 4. The recrystallized phenanthrene derivative melted at 324°–325°.

(b) 6,9-Difluoro-1H-phenanthro[9,10-d]imidazole-2-thiol:

This compound was prepared by the procedure described in Example 1; the product does not melt below 390° C.

(c) 6,9-Difluoro-2-[(1,1,2,2-tetrafluoroethyl)thio]-1H-phenanthro[9,10-d]imidazole:

The reaction with tetrafluoroethylene was carried out as described in Example 2; the pure product melted at 238°–241° C.

Anal. Calc. for $C_{17}H_8N_2F_6S$: C, 52.85; H, 2.09; N, 7.25. Found: C, 52.93; H, 2.25; N, 7.03.

EXAMPLE 8

6,9-Difluoro-2-[(1,1,2,2-tetrafluoroethyl)sulfonyl]-1H-phenanthro[9,10-d]imidazole

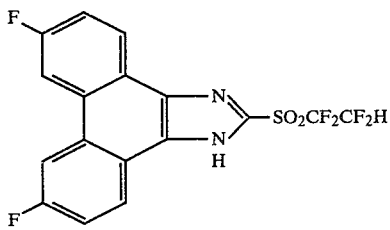

The tetrafluoroethyl derivative (Example 7) was oxidized using m-chloroperoxybenzoic acid. (Conditions described in Example 3). The pure product melts at 258°.

The following compounds can be prepared following the procedures outlined above and illustrated in the preceding examples.

Table 1

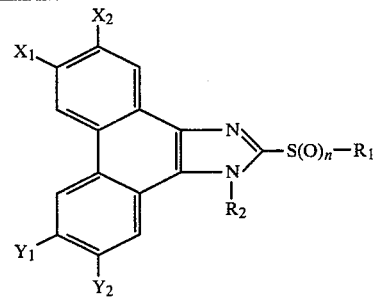

| Example No. | $X_1$ | $X_2$ | $Y_1$ | $Y_2$ |
|---|---|---|---|---|
| 9 | F | H | H | H |
| 10 | F | H | H | H |
| 11 | $(CH_3)_2N$ | H | $OCH_3$ | H |
| 12 | H | $OC_2H_5$ | H | H |
| 13 | Cl | H | H | H |
| 14 | Cl | H | Cl | H |
| 15 | H | Cl | H | Cl |
| 16 | F | H | F | H |
| 17 | $OCH_3$ | H | H | H |
| 18 | $OC_2H_5$ | H | Cl | H |
| 19 | F | H | $OCH_3$ | H |
| 20 | F | H | H | H |
| 21 | F | H | Cl | H |
| 22 | Cl | Cl | H | H |
| 23 | F | H | $OCH_3$ | H |
| 24 | F | Cl | H | H |
| 25 | Cl | Cl | Cl | H |

| Compound No. | $R_1$ | $R_2$ | n |
|---|---|---|---|
| 9 | $CF_2CHF_2$ | $COOC_2H_5$ | 0 |
| 10 | $CF_3$ | H | 1 |
| 11 | $CF_2CH_2F$ | H | 2 |
| 12 | $CF_2CHF_2$ | H | 2 |
| 13 | $CF_2CHF_2$ | H | 2 |
| 14 | $CF_2CHF_2$ | H | 2 |
| 15 | $CF_3$ | 2-tetrahydropyranyl | 0 |
| 16 | $CF_2CHF_2$ | 2-tetrahydrofuranyl | 0 |
| 17 | $CF_3$ | $COC_6H_5$ | 0 |
| 18 | $CF_3$ | $CH_2OCH_2CH_2OCH_3$ | 0 |
| 19 | $CF_2CHF_2$ | $SO_2C_6H_5$ | 0 |
| 20 | $CF_2CHF_2$ | $C(O)\text{-}C_6H_4\text{-}Cl$ | 0 |
| 21 | $CF_3$ | $C(O)\text{-}C_6H_4\text{-}Br$ | 0 |

Table 1-continued

[Structure: fused ring system with X1, X2 substituents on one ring, Y1, Y2 on another, and N-N ring with S(O)n—R1 and N-R2]

| # | | | n |
|---|---|---|---|
| 22 | CF₂CHF₂ | SO₂—⟨C₆H₄⟩—CH₃ | 0 |
| 23 | CF₃ | C(O)—⟨C₆H₄⟩—NO₂ | 0 |
| 24 | CF₃ | C(O)—⟨C₆H₄⟩—OCH₃ | 0 |
| 25 | CF₂CHF₂ | COCH₃ | 0 |

Dosage Forms

The anti-arthritic agents of this invention can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 0.05 to 50, and preferably 0.01 to 25 milligrams per kilogram per day given in divided doses 2 to 4 times a day or in sustained release form is effective to obtain desired results.

Dosage forms (compositions) suitable for internal administration contain from about 100 milligrams to about 10 grams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose, derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroeum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P.

XV and adjusting the pH of the solution to between 6 and 7. The solution is sterilized by filtration.

Testing for Pharmaceutical Utility

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2 1973 "Models Used for the Study and Therapy of Rheumatoid Arthritis'—Symposium of the American Society for Pharmacology and Experimental Therapeutics—states "The rat polyarthritis produced by intradermal injection of a suspension of Mycobacterium tuberculosis in mineral oil (adjuvant) has been used extensively for the screening of drugs of potential use in rheumatoid arthritis".

Charles River Lewis male rats (130-150 grams) were injected subcutaneously in the planter area of the right hind paw with 0.1 ml of adjuvant (Difco heat-killed, lyophilized *Mycobacterium butyricum* suspended in mineral oil 5 mg/ml). 20 Nonarthritic controls were injected with mineral oil. The animals were held for two weeks to allow development of arthritis. Paw volumes (uninjected, left hind paw) were measured and the adjuvant injected rats were culled and distributed to treatment groups of 10 of equal disease severity. Nonarthritic controls were distributed to two groups of 10. The rats were given oral doses of compound or PVA-Acacia (Polyvinyl Alcohol 1%, Gum Acacia, U.S.P. 5%, Methylparaben 0.5%) (10 ml/kg) by gavage on that day and on the six following days. One day after the last dose the paw volumes (uninjected, left hind paw) were measured using a Ugo Basile Volume Differential Meter Model 7101.

$$\frac{\text{Arthritic Control} - \text{Treatment Group}}{\text{Arthritic Control} - \text{Non-Arthritic Control}} \times 100 =$$
Mean Paw Volume (ml) − Mean Paw Volume (ml)
% Decrease from Control Mean Paw Volume Dose-response regression lines of the percent decrease were plotted on semi-log paper by visual fit and the ED50% decrease from control paw volume was determined by inspection. Data for compounds of this invention are summarized in Table 2 hereinbelow and compared with other well-known anti-inflammatory agents.

Table 2

| Compound | Established Adjuvant-Induced Arthritis in Rats (A.A.) A.A. ED50%* mg/kg |
|---|---|
| Example 2 | >25 |
| 3 | 28 |
| 7 | 0.45 (1.6) |
| 8 | 0.8 |
| Indomethacin | 0.3 |
| Phenylbutazone | 10 |
| Ibuprofen | 100 |
| Aspirin | 305 |

*Determined as % paw volume reduction from control.

A procedure for detecting and comparing the analgesic activity of compounds in this series and standard drugs for which there is a good correlation with human efficacy is the phenylquinone writhing test.

The phenylquinone writhing test, modified from Siegmund, et al., *Proc. Soc. Exp. Biol. Med.* 95, 729 (1957), was employed. A test compound suspended in 1% methylcellulose was given orally to fasted (17-21 hours) female white mice, 5-20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice (ED$_{50}$) was calculated by the moving average method of Thompson, W. R., *Bact. Rev.* 11, 115-145 (1947).

The analgesic data for a compound of this invention are summarized in Table 3.

Table 3

| Phenylquinone Writhing Test | |
|---|---|
| Compound | ED50* |
| Example 6 | 29 |

*Units are in mg/kg at 2 hours.

What is claimed is:

1. A compound of the formula wherein
n=0-2
$R_1$ = —CF$_2$H, —CF$_3$ or —CF$_2$CH$_m$F$_{3-m}$ in which m=0-3
$R_2$ = —H, $$-\underset{R_3}{\underset{|}{C}}HOR_4,$$

2-tetrahydropyranyl, 2-tetrahydrofuranyl,

—COR$_5$, —CR$_5$,
$$\underset{Y_3}{-\overset{O}{\underset{\|}{C}}-\bigcirc} \text{ or } -SO_2-\underset{Y_3}{\bigcirc};$$

provided when R$_2$=

—C—OR$_5$, —C—R$_5$,
$$\underset{Y_3}{-\overset{O}{\underset{\|}{C}}-\bigcirc} \text{ or } -SO_2-\underset{Y_3}{\bigcirc},$$

then n=0;
R$_3$ = —H or —CH$_3$;

$R_4 =$ $C_{1-3}$ alkyl, benzyl, $-CH_2CH_2OCH_3$ or

$R_5 = C_{1-4}$ alkyl or benzyl;

$X_1$ and $Y_1$ are independently selected from the group consisting of $-H$, $-F$, $-Cl$, dimethylamino and $C_{1-2}$ alkoxy;

$X_2$ and $Y_2$ are independently selected from the group consisting of $-H$, $-F$ and $-Cl$;

$Y_3$ is $-H$, $-F$, $-Cl$, $-Br$, $C_{1-4}$ alkyl, $C_{1-4}$ alkoxy or $-NO_2$;

and, when $R_2 = -H$, a pharmaceutically suitable acid salt when $n = 0$ or pharmaceutically suitable metal salts when $n = 1-2$.

2. A compound of claim 1 in which $n = 2$.

3. A compound of claim 1 in which $R_1$ is either $-CF_3$ or $-CF_2CF_2H$.

4. A compound of claim 1 in which $R_2 = H$.

5. A compound of claim 1 in which $X_1$ and $Y_1$ are independently selected from the group consisting of $-H$, $-F$, $-Cl$ and $-OCH_3$, provided, however, that $X_1$ and $Y_1$ are not both $-H$.

6. A compound of claim 1 in which $X_2$ and $Y_2$ are both $-H$.

7. A compound of claim 1 in which $n=2$, $R_2=H$, $X_2$ and $Y_2$ are both $-H$, $R_1$ is either $-CF_3$ or $-CF_2CF_2H$ and $X_1$ and $Y_1$ are independently selected from the group consisting of $-H$, $-F$, $-Cl$ and $-OCH_3$, but $X_1$ and $Y_1$ are not both $-H$.

8. A pharmaceutical composition comprising a pharmaceutically suitable carrier and a compound of claim 1 in an amount sufficient to provide anti-inflammatory activity in mammals.

9. A pharmaceutical composition comprising a pharmaceutically suitable carrier and a compound of claim 2 in an amount sufficient to provide anti-inflammatory activity in mammals.

10. A pharmaceutical composition comprising a pharmaceutically suitable carrier and a compound of claim 3 in an amount sufficient to provide anti-inflammatory activity in mammals.

11. A pharmaceutical composition comprising a pharmaceutically suitable carrier and a compound of claim 4 in an amount sufficient to provide anti-inflammatory activity in mammals.

12. A pharmaceutical composition comprising a pharmaceutically suitable carrier and a compound of claim 5 in an amount sufficient to provide anti-inflammatory activity in mammals.

13. A pharmaceutical composition comprising a pharmaceutically suitable carrier and a compound of claim 6 in an amount sufficient to provide anti-inflammatory activity in mammals.

14. A pharmaceutical composition comprising a pharmaceutically suitable carrier and a compound of claim 7 in an amount sufficient to provide anti-inflammatory activity in mammals.

15. A method for reducing inflammation in mammals comprising administering to the mammal an amount of a compound of claim 1 sufficient to provide anti-inflammatory activity therein.

16. A method for reducing inflammation in mammals comprising administering to the mammal an amount of a compound of claim 2 sufficient to provide anti-inflammatory activity therein.

17. A method for reducing inflammation in mammals comprising administering to the mammal an amount of a compound of claim 3 sufficient to provide anti-inflammatory activity therein.

18. A method for reducing inflammation in mammals comprising administering to the mammal an amount of a compound of claim 4 sufficient to provide anti-inflammatory activity therein.

19. A method for reducing inflammation in mammals comprising administering to the mammal an amount of a compound of claim 5 sufficient to provide anti-inflammatory activity therein.

20. A method for reducing inflammation in mammals comprising administering to the mammal an amount of a compound of claim 6 sufficient to provide anti-inflammatory activity therein.

21. A method for reducing inflammation in mammals comprising administering to the mammal an amount of a compound of claim 7 sufficient to provide anti-inflammatory activity therein.

* * * * *